(12) United States Patent
Reed et al.

(10) Patent No.: US 8,007,427 B2
(45) Date of Patent: Aug. 30, 2011

(54) PRODUCTS AND METHODS FOR BRACHYTHERAPY

(75) Inventors: Jay Reed, Elk Grove Village, IL (US); Mike Rapach, Carpentersville, IL (US); Kevin Helle, Barlett, IL (US); Juliano Oei, Chicago, IL (US)

(73) Assignee: Medi-Physics, Inc., Princeton, NJ (US)

( * ) Notice: Subject to any disclaimer, the term of this patent is extended or adjusted under 35 U.S.C. 154(b) by 812 days.

(21) Appl. No.: 11/959,687

(22) Filed: Dec. 19, 2007

(65) Prior Publication Data
US 2008/0097140 A1    Apr. 24, 2008

Related U.S. Application Data

(62) Division of application No. 10/390,506, filed on Mar. 17, 2003, now Pat. No. 7,322,928.

(51) Int. Cl.
*A61M 36/00* (2006.01)
(52) U.S. Cl. .......................................................... 600/7
(58) Field of Classification Search ................... 600/1–8
See application file for complete search history.

(56) References Cited

U.S. PATENT DOCUMENTS

| | | |
|---|---|---|
| 2,668,162 A | 2/1954 | Lowe |
| 2,703,316 A | 3/1955 | Schneider |
| 2,758,987 A | 8/1956 | Salzberg |
| 3,297,033 A | 1/1967 | Schmitt et al. |
| 3,351,049 A | 11/1967 | Lawrence |
| 3,636,956 A | 1/1972 | Schneider |
| 3,839,297 A | 10/1974 | Wasserman et al. |
| 4,141,087 A | 2/1979 | Shalaby et al. |
| 4,323,055 A | 4/1982 | Kubiatowicz |
| 4,441,496 A | 4/1984 | Shalaby et al. |
| 4,452,973 A | 6/1984 | Casey et al. |
| 4,473,670 A | 9/1984 | Kessidis |
| 4,502,988 A | 3/1985 | Hatfield |
| 4,509,506 A | 4/1985 | Windorski et al. |
| 4,612,923 A | 9/1986 | Kronenthal |
| 4,646,741 A | 3/1987 | Smith |
| 4,689,424 A | 8/1987 | Shalaby et al. |
| 4,702,228 A | 10/1987 | Russell et al. |
| 4,741,337 A | 5/1988 | Smith et al. |
| 4,784,116 A | 11/1988 | Russell et al. |
| 4,916,209 A | 4/1990 | Fung et al. |
| 5,015,677 A | 5/1991 | Benedict |

(Continued)

FOREIGN PATENT DOCUMENTS

WO     00/64538     11/2000

(Continued)

OTHER PUBLICATIONS

International Search Report and written Opinion of the International Search Authority for PCT/US2004/008084 dated Jul. 20, 2004.

(Continued)

*Primary Examiner* — Samuel G Gilbert
(74) *Attorney, Agent, or Firm* — Robert F. Chisholm

(57) ABSTRACT

A radioactive member for use in brachytherapy comprising a hollow elongate bioabsorbable suture member with radioactive seeds and spacer members without different coloration and diameter from the radioactive seeds alternately disposed therein, and methods for the manufacture and the use thereof. The radioactive members may be used in the treatment of, for example, prostate cancer.

11 Claims, 6 Drawing Sheets

U.S. PATENT DOCUMENTS

| | | | |
|---|---|---|---|
| 5,264,540 | A | 11/1993 | Cooper et al. |
| 5,404,309 | A | 4/1995 | Yamamoto et al. |
| 5,460,592 | A | 10/1995 | Langton et al. |
| 5,521,280 | A | 5/1996 | Reilly et al. |
| 5,648,095 | A | 7/1997 | Illum et al. |
| 5,741,522 | A | 4/1998 | Violante et al. |
| 5,776,496 | A | 7/1998 | Violante et al. |
| 5,938,583 | A | 8/1999 | Grimm |
| 6,264,600 | B1 | 7/2001 | Grimm |
| 6,422,989 | B1 | 7/2002 | Hektner |
| 6,572,525 | B1 * | 6/2003 | Yoshizumi ............ 600/7 |
| 6,679,824 | B1 * | 1/2004 | Reed et al. ............ 600/7 |
| 6,749,554 | B1 | 6/2004 | Snow et al. |
| 7,118,523 | B2 * | 10/2006 | Loffler et al. ............ 600/3 |
| 2002/0055666 | A1 | 5/2002 | Hunter et al. |

FOREIGN PATENT DOCUMENTS

| | | | |
|---|---|---|---|
| WO | WO 00/64538 | * | 11/2000 |
| WO | 02/36199 | | 5/2002 |
| WO | 2004/026222 | | 4/2004 |

OTHER PUBLICATIONS

J.C. Blasco—The Urological Clinics of North America (1996).
H. Ragde—Cancer 80, 442-453 (1997).
Tapen—Int. Radiation Oncology Biol. Phys. vol. 42(5) pp. 1063-1067 (1998).
Chemical Engineering News, Dec. 8, 1997, 75 (49) p75.
Proc. IUPAC, I.U.P.A.C., Macromol. Symp., 28th (1982) 395.
Proc. SPIE-Int. Soc. Opt. Eng. (1998) 3258, 164-168.
Van't Riet, International Journal of Radiation Oncology Biol. Phys. vol. 24 pp. 555-558 (1992).

* cited by examiner

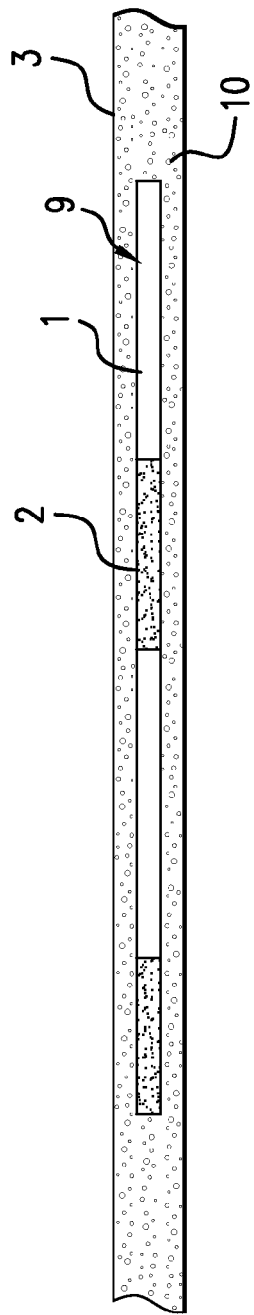
FIG.5
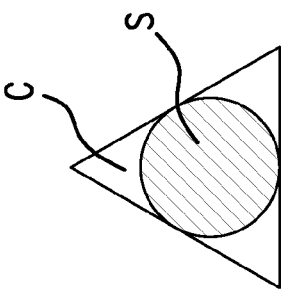
FIG.6A
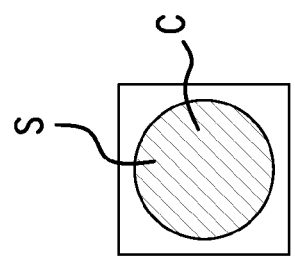
FIG.6B
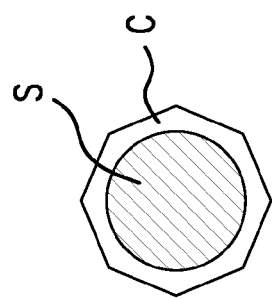
FIG.6C
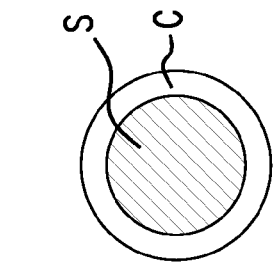
FIG.6D
FIG.6E

PRODUCTS AND METHODS FOR BRACHYTHERAPY

This application is a divisional of U.S. patent application Ser. No. 10/390,506 filed Mar. 17, 2003, now U.S. Pat. No. 7,322,928 the entire disclosure of which is hereby incorporated by reference.

FIELD OF INVENTION

The present invention relates generally to radiotherapy. More specifically, it relates to radioactive sources for use in brachytherapy and to methods for the preparation of such sources.

BACKGROUND OF THE INVENTION

Brachytherapy is a general term covering medical treatment which involves the placement of a radioactive source near a diseased tissue and may involve the temporary or permanent implantation or insertion of a radioactive source into the body of a patient. The radioactive source is thereby located in proximity to the area of the body which is being treated. This has the advantage that a high dose of radiation may be delivered to the treatment site with relatively low dosages of radiation to surrounding or intervening healthy tissue.

Brachytherapy has been proposed for use in the treatment of a variety of conditions, including arthritis and cancer, for example breast, brain, liver and ovarian cancer and especially prostate cancer in men (see for example J. C. Blasko et al., *The Urological Clinics of North America*, 23, 633-650 (1996), and H. Ragde et al., *Cancer*, 80, 442-453 (1997)). Prostate cancer is the most common form of malignancy in men in the USA, with more than 44,000 deaths in 1995 alone. Treatment may involve the temporary implantation of a radioactive source for a calculated period, followed by its removal. Alternatively, the radioactive source may be permanently implanted in the patient and left to decay to an inert state over a predictable time. The use of temporary or permanent implantation depends on the isotope selected and the duration and intensity of treatment required.

Permanent implants for prostate treatment comprise radioisotopes with relatively short half lives and lower energies relative to temporary sources.
Examples of permanently implantable sources include iodine-125 or palladium-103 as the radioisotope. The radioisotope is generally encapsulated in a casing such as titanium to form a "seed" which is then implanted. Temporary implants for the treatment of prostate cancer may involve iridium-192 as the radioisotope.

Conventional radioactive sources for use in brachytherapy include so-called seeds, which are sealed containers, for example of titanium, containing the radioisotope within a sealed chamber but permitting radiation to exit through the container/chamber walls (U.S. Pat. No. 4,323,055 and U.S. Pat. No. 3,351,049). Such seeds are only suitable for use with radioisotopes which emit radiation which can penetrate the chamber/container walls. Therefore, such seeds are generally used with radioisotopes which emit γ-radiation or low-energy X-rays, rather than with β-emitting radioisotopes.

Radioactive seeds are generally loaded into needles, with the needles then being inserted into the treatment site, such as prostate, using ultrasound imaging to guide the insertion process. The radioactive seeds are either positioned independently within the needles and hence are located independently within the treatment site after they have been moved out of the needle, or they are connected in a string arrangement by being loaded within a hollow, absorbable suture member.

U.S. Pat. No. 5,460,592 discloses a method and apparatus for transporting a radioactive device. The device comprises a flexible, elongated woven or braided bio-absorbable carrier material having spaced radioactive seeds disposed therein. On heating, the carrier material holding the seeds becomes semi-rigid. A length of the semi-rigid carrier material with radioactive seeds disposed therein may then be loaded into a conventional, hollow metal dispensing needle or applicator cartridge which is used to implant the radioactive seeds into or contiguous to the treatment site, for example a tumour.

A commercial product consisting of iodine-125 seeds regularly spaced at between 0.6 and 1.2 cm centre to centre inside a braided, semi-rigid bioabsorbable suture material is available from Medi-Physics Inc. under the trade name I-125 RAPID Strand™. This product may be used to treat conditions such as head and neck cancers, including those of the mouth, lips and tongue, brain tumours, lung tumours, cervical tumours, vaginal tumours and prostate cancer.

One advantage of this type of suture/radioactive seed combination is that the radioactive seeds are implanted or inserted into a patient with a pre-determined spacing, depending on their spacing in the suture material. The bioabsorbable material is then slowly absorbed into the patient's body to leave the spaced seeds in position. This predetermined spacing and the semi-rigid nature of the suture aids a physician in calculating both the total radiation dose and the dose profile which will be delivered by the seeds inside a patient's body, and also aids in accurate placement of the seeds. In addition, more than one seed is implanted at once, so lessening the time taken for implantation over that required for the placement of individual loose seeds. The risk of seed migration away from the site of implantation is also reduced (Tapen et al., *Int. J. Radiation Oncology Biol. Phys.*, vol. 42(5), pages 1063-1067, 1998).

Another advantage of the hollow suture combination over independent seeds approach is that the independent seeds, even once in the treatment site, for example prostate, could migrate out of the prostate to various other locations in the body, including lungs. Migrated seeds can reduce implant quality and also potentially harm the patient.

However, this hollow suture combination has limitations on long axis strength due to the void areas, introduced into the arrangement during manufacturing, used for the spacing between the radioactive seeds. This void area long axis strength is limited to the strength of the suture material. Although the void area strength is increased during the heat stiffening manufacturing process, the resulting strength is still not ideal. Due to this limitation, the suture combination can sometimes jam within the insertion needle, resulting in a collapsing of the suture combination in the void area between the radioactive seeds. This condition requires removal of the needle from the prostate and the subsequent reloading of the needle with independent radioactive seeds. This alteration of technique is time-consuming and expensive in nature.

One approach to remedy the situation is disclosed in U.S. Pat. No. 6,264,600. It discloses a method and apparatus including a hollow suture with alternating plurality of radioactive seeds and intermediate spacers. While this suture/seed combination offers stronger long axis strength, there are several areas that can be improved upon.

First, there is still need for even more long axis strength to reduce the possibilities of suture jamming within the insertion needle.

Further, both hollow suture/seed combination and current hollow suture/seed/spacer combination is singular in color, with only dimensional differences in seeds and void areas of the assembly. This limitation can cause uncertainty in preparing the combination in implant. The current fixture only allows cutting in the void areas of the suture combination, away from the critical radioactive seed component. However, this becomes impossible once the suture combination is removed from the fixture.

Finally, current suture/seed/spacer combination has similar diameters for both seed and spacer. This lack of dimensional difference makes cutting more difficult.

There is therefore a need for an improved radioactive source which does not suffer from all the disadvantages of the known sources, and which can preferably be produced using an automated manufacturing process.

SUMMARY OF THE INVENTION

In one aspect of the invention there is therefore provided a radioactive member for use in brachytherapy comprising a hollow elongate bioabsorbable suture member with a plurality of radioactive seeds and spacer members disposed alternately therein, wherein the spacer members are dyed with a different color from that of the undyed radioactive seeds and of different diameter from that of the radioactive seeds. The radioactive seeds and the spacer members are preferably retained therein by deformation of the suture member on heating, followed by subsequent cooling.

In a further aspect of the invention, there is provided a radioactive member for use in brachytherapy comprising a hollow elongate bioabsorbable suture member with one or more slots therein in which one or more radioactive seeds and spacer members are disposed alternately in a spaced relationship, wherein the spacer members are dyed with a different color from that of the undyed radioactive seeds and of different diameter from that of the radioactive seeds. Preferably, the suture member is essentially stiff. The slots may comprise a continuous groove or a series of discrete openings longitudinally spaced along the suture material. Preferably, the radioactive seeds and spacers are securely retained in the suture member by heat sealing.

As a further feature of the invention there is provided a method for the production of a radioactive member for use in brachytherapy comprising an elongate, bioabsorbable suture member with radioactive seeds and spacer members disposed alternately therein, said method comprising the steps of:
a) providing a hollow bioabsorbable suture member,
b) providing a plurality of radioactive seeds,
c) providing a plurality of bioabsorbable spacer members, wherein the spacer members are dyed with a different color from that of the undyed radioactive seeds and of different diameter from that of radioactive seeds,
d) heating the radioactive seeds to a temperature above the melting or softening temperature of the suture material,
e) placing the heated seeds and spacer members alternately onto the suture member in a predetermined pattern whereby the suture member melts or deforms around each source and spacer member, and
f) cooling the suture member such that it solidifies or hardens about each source and spacer member so as to securely retain each source in place.

In an alternative embodiment of the method, in steps d) and e), the suture member may itself be at an elevated temperature (at which it does not lose its integrity), for example following extrusion, and the radioactive seeds and spacer members then placed onto the suture member such that they are held in place as it cools. In such a method, the radioactive seeds may be cold or may themselves also be heated.

In step e), an external force may also optionally be applied to deform or to further deform the suture member around the radioactive seeds and the spacer members. For example, heated plates may be applied to the exterior of the suture member to further melt the suture member around the radioactive seeds and the spacer members to hold them in place.

In yet another embodiment of the method, it further comprises a step of sterilizing the radioactive member.

In another embodiment of the invention, there is provided a method of using the radioactive member for brachytherapy, said method comprising:
a) cutting the radioactive member at one of the spacer members to a prescribed length according to the prescribed implant plan;
b) inserting the cut radioactive member into a hub end of a hollow insertion needle suitable for insertion into a prescribe treatment area, so that the entire radioactive member is inside the needle;
c) pushing the radioactive member through the hollow insertion needle with a needle stylet, until the leading tip of the radioactive member reaches a needle plugging media;
d) inserting the loaded insertion needle into the prescribed treatment area of a patient;
e) removing the insertion needle from around the radioactive member, leaving the radioactive member in the prescribed treatment area of the patient.

In yet another embodiment of the invention, there is provided another method of using the radioactive member for brachytherapy, said method comprising:
a) inserting an insertion needle into a prescribed treatment area of a patient;
b) cutting the radioactive member at one of the spacer members to a prescribed length according to the prescribed implant plan;
c) loading the radioactive member into an after-loading device;
d) transferring the radioactive member in the after-loading device to the insertion needle where it mates into the insertion needle hub;
e) applying a stylet to advance the radioactive member through the after-loading device into the insertion needle, and finally into the patient;
f) removing the insertion needle and the after-loading device.

BRIEF DESCRIPTION OF THE DRAWINGS

FIG. 5 depicts an alternate embodiment of the improved suture combination of the present invention.

FIGS. 6A-E depict cross-sectional views of various improved suture combinations of the present invention.

DETAILED DESCRIPTION OF THE INVENTION

Figure 1:
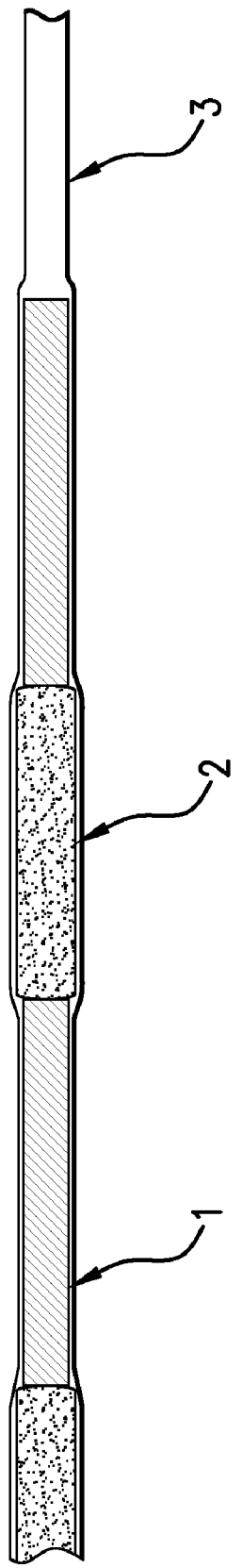
FIG. 1 is a cross-sectional view of the improved suture combination of the present invention.

Referring to the drawings, FIG. 1 shows a cross-section of one embodiment of the invention: a radioactive member for use in brachytherapy comprising a hollow elongate bioabsorbable suture member 3 with radioactive seeds 2 and spacer members 1 alternately dispersed therein.

Radioactive seeds 2 are typically 0.5 mm to 1 mm in diameter and 4 mm to 5 mm in length. However, dimensions of radioactive seeds can vary. The spacer members can be of fixed or variable length between each radioactive seed. The spacer members are on both the leading and trailing edges of the radioactive member.

Coloration in spacer members may be used to create a color scheme to easily identify components inside the suture member. Spacer members 1 may be dyed, for example, violet, to distinguish from undyed suture member 3. Diameter size of the spacer members 1, in comparison to diameter size of the radioactive seeds 2, may be different, such as reduced, to easily identify components inside the suture member 3. Heat stiffening of the radioactive member during the manufacturing process increases the long axis rigidity, adheres the suture member 3 to the internal radioactive seeds 2 and spacer members 1, and allows coloration to transfer from the spacer members 1 to suture member 3 for easy identification of components.

The suture member and spacer member can be made of the same material. They may be any non-toxic, bio-compatible, bioabsorbable material or a mixture of such materials. As used herein, a bioabsorbable material is any material of which a substantial portion will be metabolized within a patient's body and ultimately eliminated therefrom. Suitable bioabsorbable materials include poly(glycolic acid) (PGA) and poly(lactic acid) (PLA), polyester amides of glycolic or lactic acids such as polymers and copolymers of glycolate and lactate, polydioxanone and the like. Such materials are more fully described in U.S. Pat. No. 5,460,592 which is hereby incorporated by reference. Suitable commercially available polymers include polyglycaprone 25 (MONCRYL™), polyglactin 910 (VICRYL™) and polydioanone (PDS II), all available from Ethicon, Inc. of New Jersey, U.S.A.

Other suitable bioabsorbable polymers and polymer compositions that may be used in this invention are described in the following patents which are hereby incorporated by reference: U.S. Pat. No. 4,052,988 which discloses compositions comprising extruded and oriented filaments of polymers of p-dioxanone and 1,4-dioxepan-2-one; U.S. Pat. No. 3,839,297 which discloses compositions comprising poly[L(−)lactide-co-glycolide] suitable for use as absorbable sutures; U.S. Pat. No. 3,297,033 which discloses the use of compositions comprising polyglycolide homopolymers as absorbable sutures; U.S. Pat. No. 2,668,162 which discloses compositions comprising high molecular weight polymers of glycolide with lactide; U.S. Pat. No. 2,703,316 which discloses compositions comprising polymers of lactide and copolymers of lactide with glydolide; U.S. Pat. No. 2,758,987 which discloses compositions comprising optically active homopolymers of L(−) lactide i.e. poly L-Lactide; U.S. Pat. No. 3,636,956 which discloses compositions of copolymers of L(−) lactide and glycolide having utility as absorbable sutures; U.S. Pat. No. 4,141,087 which discloses synthetic absorbable crystalline isomorphic copolyoxylate polymers derived from mixtures of cyclic and linear diols; U.S. Pat. No. 4,441,496 which discloses copolymers of p-dioxanone and 2,5-morpholinediones; U.S. Pat. No. 4,452,973 which discloses poly(glycolic acid)/poly(oxyalkylene) ABA triblock copolymers; U.S. Pat. No. 4,510,295 which discloses polyesters of substituted benzoic acid, dihydric alcohols, and glycolide and/or lactide; U.S. Pat. No. 4,612,923 which discloses surgical devices fabricated from synthetic absorbable polymer containing absorbable glass filler; U.S. Pat. No. 4,646,741 which discloses a surgical fastener comprising a blend of copolymers of lactide, glycolide, and poly(p-dioxanone); U.S. Pat. No. 4,741,337 which discloses a surgical fastener made from a glycolide-rich blend of polymers; U.S. Pat. No. 4,916,209 which discloses bioabsorbable semi-crystalline depsipeptide polymers; U.S. Pat. No. 5,264,540 which discloses bioabsorbable aromatic polyanhydride polymers; and U.S. Pat. No. 4,689,424 which discloses radiation sterilizable absorbable polymers of dihydric alcohols.

Bioabsorbable polymers and polymer compositions are especially useful when they comprise bioabsorbable fillers such as those described in U.S. Pat. No. 4,473,670 (which is incorporated by reference) which discloses a composition of a bioabsorbable polymer and a filler comprising a poly(succinimide); and U.S. Pat. No. 5,521,280 (which is incorporated by reference) which discloses bioabsorbable polymers and a filler of finely divided sodium chloride or potassium chloride. Such fillers can provide increased stiffness to bioabsorbable polymers and polymer compositions.

Poly(glycolic acid) has a melting point of either 230° C. to 260° C. and a glass transition point of 45° C. to 50° C. (Materials Safety Data Sheet, Medisorb Lactide/Glycolide Polymers). If this is used as the suture material, then in steps d) and e) of the methods of the invention the sources, the spacer member and/or the suture member should be heated to at least this glass transition point temperature.

The bioabsorbable material should preferably maintain its integrity once implanted for from about 1 to 14 days. This helps to ensure that the spacing of the sources is maintained for at least a short period post-implantation. Use of the radioactive members of the invention also helps ensure proper dosimetry and minimizes source movement or shedding. Preferably the suture member should be fully absorbed by living tissue over a total of about 70 to 120 days.

By "essentially stiff" is meant that the suture member and the spacer member should have some structural integrity and be stiff enough for its proposed uses. The suture member and spacer member should be stiff enough to maintain the spacing between the radioactive seeds during storage, shipment and implantation of the radioactive member. If the suture member and spacer member have melted and deformed when heated by the seeds so as to trap the radioactive seeds in place, it should then re-stiffen when cooled.

In addition, the suture member should be formable into an elongate shape. Preferably, once in an elongate shape, the suture member and the spacer member should be easy to cut using for example a scalpel or the like. Preferably, diameter of the spacer members is different from that of the radioactive seeds, so that the spacer member can be easily identified inside the suture material. For example, diameter of the spacer members can be 0.1 mm to 0.5 mm smaller than that of the radioactive seeds. Coloration in spacer members, such as violet, may be used to create a color scheme to easily identify components inside the suture member. Dyed spacer members can be easily distinguished from undyed suture member. The suture member should also preferably have an appreciable shelf life without the need for any special storage or handling conditions. The suture member should also be sterilizable by any conventional sterilisation method, such as for example using steam, dry heat, ethylene oxide, electron-beam or gamma-radiation, as well as pulse-light sterilization method. Preferred sterilization method is ethylene oxide.

The suture member should have an internal diameter sufficient to accommodate the radioactive seeds and spacer members. As depicted in FIGS. 6A-6E, where 'S' depicts a seed or spacer and 'C' depicts the suture or carrier material, the suture member of the present invention may be of any suitable cross-section, for example substantially circular (FIG. 6B), substantially circular with at least one flattened surface (FIG. 6A), or substantially polygonal, for example, square (FIG. 6D) or triangular (FIG. 6E). A preferred suture according to the invention has a substantially square cross-section, both for ease of manufacture and to limit the surface area of the suture which will be in contact with the inside of the dispensing needle, so making jamming of the suture within the needle due to friction between the needle and the surface of the suture less likely. Reduced friction could also be achieved with any cross-section having at least one flat surface e.g. a substantially circular cross-section flattened at a region on the circumference to give a flat surface. Suitable sutures are substantially polygonal in shape, for example, hexagonal, octagonal, or 12 or 16-sided etc. Thus, another preferred suture in accordance with the invention is substantially octagonal (FIG. 6C). A substantially triangular cross-section is also preferred, as it offers one less edge than a substantially square cross-section to contact the inner walls of a delivery needle device.

The length of the suture member can vary. Preferably, a radioactive member contains 2 to 15 radioactive seeds.

Figure 7:
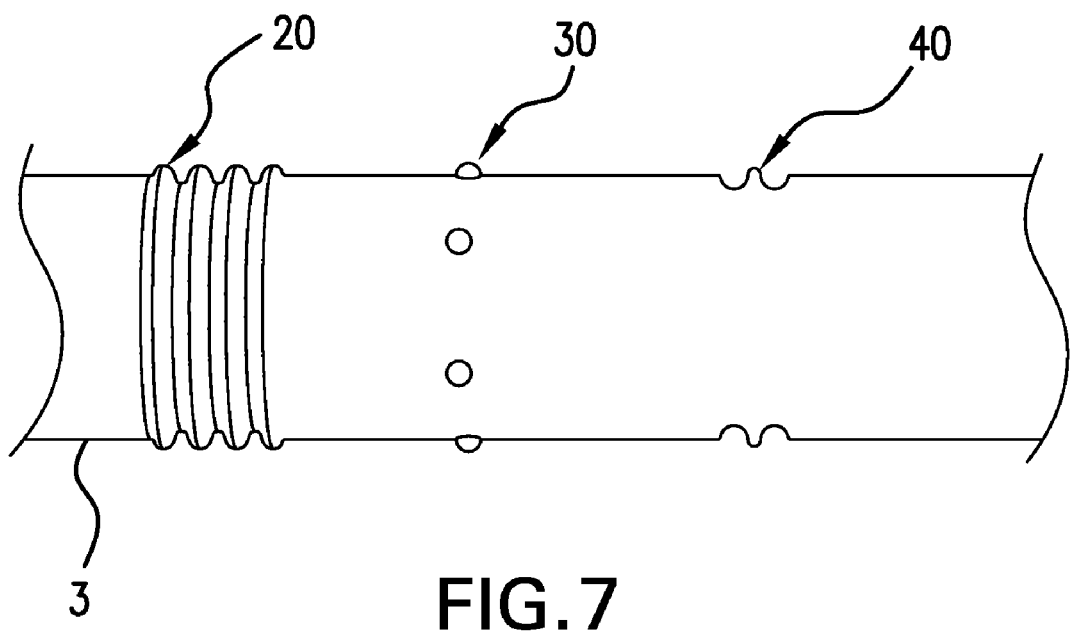
FIG. 7 depicts alternative embodiments of the features for the outer surface of a member of the present invention.

The surface contact between the inner surface of a needle or other delivery device and a suture of any cross sectional shape can be further minimized by the provision of suitable surface structures on the suture surface which contacts the delivery device. For example, as depicted in FIG. 7, in the case of a curved suture surface, surface contact can be reduced by incorporating ridges 20, spheres 30, or other protrusions 40 in the area of the suture surface that contacts the needle or delivery device surface. Preferably, these surface structures comprise biocompatible or biodegradable suture material. A suitable method for forming such surface structures comprises application of a heated mould or press plate, the surface of which is configured as a negative of the structures being applied to the suture. Upon application of the heated mould to the surface of the suture, the suture will flow into the cavities in the negative mould. Release of the suture from the mould and cooling of the suture will impart to the suture surface a positive image, reciprocal to the negative image of the mould. Beads or bumps produced on the surface of the suture provide reduced contact area and less friction between the suture and a needle used as a delivery device.

Preferably, the suture will be visible using ultrasound imaging techniques. For example, as shown in FIG. 5, it may comprise sound reflecting particles or bubbles of gas, generally represented as "10", which serve to enhance its ultrasound visibility. If the suture is a polymer, bubbles of gas may be trapped in the polymer during the extrusion process to form a suture, for example by blowing bubbles into the polymer as it is extruded. Alternatively, the polymer may be agitated (e.g. by sonication) prior to extrusion under a suitable gas atmosphere such that bubbles of gas are incorporated therein. Suitable gases include air, nitrogen, carbon dioxide, Freons™ and fluorocarbons such as perfluorobutane.

Alternatively, the suture member may be subjected to a gas under pressure, for example greater than atmospheric pressure, immediately prior to extrusion such that the gas becomes dissolved into the material. Upon extrusion combined with a reduction in the pressure of gas due to warming (such as on extrusion into an ambient pressure and temperature environment), the gas will expand to form bubbles in the suture member. Preferably, the bubbles are at or near the surface of the suture member.

The suture can be uniformly visible or non-uniformly visible by ultrasound. For example, some regions of the suture may be more visible by ultrasound than other regions. This can arise due to the presence of regions where clusters of sound reflecting gas bubbles or particles reside in a suture.

The suture may additionally or alternatively comprise particles which serve to enhance its visibility to ultrasound. Suitable particles include particles of metal (for example titanium or aluminium), glass, silica, iron oxide, sand, clay, plastics such as TEFLON™, porous uniformly-sized non-aggregated particles as described in U.S. Pat. No. 5,741,522 and U.S. Pat. No. 5,776,496 which are hereby incorporated by reference, hollow microcapsules or solid microspheres such as those disclosed in U.S. Pat. No. 5,648,095 which is hereby incorporated by reference, and microspheres of a fused sugar, a fused amino acid or of PEG (polyethylene glycol).

One advantage of using imaging-visible, for example ultrasound-visible, radioactive members of the invention in brachytherapy is that the signal and image may be read, measured and analysed by suitable computer software sufficiently quickly to allow a physician to plan real-time dosimetry. This is advantageous from a clinical view point for both patient and medical personnel. However, the members of the invention may be used in processes involving any type of dosimetry mapping that uses information obtained due to the imaging visibility of the radioactive seeds.

In addition, a physician may use the same imaging technique, for example ultrasound, already in place during surgery to confirm both organ (e.g. prostate) position and size, and radioactive seeds placement. This could enable a physician to calculate if additional radioactive seeds need to be inserted, for example in situations where the dose pattern needs to be recalculated based on the actual, implanted position of the sources.

The overall dimensions of the suture member should be such that it will fit inside a dispensing needle or applicator cartridge. For example, if the internal diameter of a thin walled 18 gauge needle is 0.102 cm (0.040 inches), then the effective maximum diameter of the suture is preferably less than 0.102 cm (0.040 inches), so that it can be dispensed from such needles.

The suture can be uniformly or non-uniformly distributed cross-sectionally around the sources. For example where the sources are substantially cylindical radioactive seeds, the shape of the cross-section of the internal surface of the suture could, preferably be substantially round. In an alternative embodiment, the surface could be substantially square.

Any conventional radioactive seed may be used as the radioactive source. These include for example the radioactive seeds disclosed in U.S. Pat. No. 5,404,309, U.S. Pat. No. 4,784,116, U.S. Pat. No. 4,702,228, U.S. Pat. No. 4,323,055 and U.S. Pat. No. 3,351,049 which are hereby incorporated by reference. By "seed" is meant any sealed container, for example a metal container, containing or encapsulating a radioisotope. Suitable biocompatible container materials include metals or metal alloys such as titanium, gold, platinum and stainless steel; plastics such as polyesters and vinyl polymers, and polymers of polyurethane, polyethylene and poly(vinyl acetate); composites such as graphite; glass such as matrices comprising silicon oxide, and any other biocompatible material. Titanium and stainless steel are preferred materials for the containers.

The radioactive seeds may also comprise a suitable radioisotope encapsulated within a polymer or ceramic matrix.

Typical radioactive seeds are substantially cylindrical in shape. Dimensions of a typical seed can be approximately 4.5 mm long with a diameter of approximately 0.8 mm.

Any radioisotope suitable for use in brachytherapy may be used in the radioactive seeds. Non-limiting examples include palladium-103, iodine-125, strontium-89, sulphur-35, cesium-131, gold-198, thulium-170, chromium-56, arsenic-73, yttrium-90, phosphorus-32 and mixtures thereof. Especially preferred are palladium-103 and iodine-125. More than one type of radioisotope may be present in the radioactive seeds for use in the invention.

The radioactive seeds and spacer members are preferably loaded linearly along the longest axis of the elongate suture member. The orientation of the radioactive seeds relative to the suture will depend on the overall size and shape of the suture and the radioactive seeds. If the radioactive seeds are substantially cylindrical in shape, for example if they are conventional seeds, then they are preferably orientated with their longitudinal axes parallel to the longitudinal axis of the elongate suture itself. Preferably, the radioactive seeds are regularly spaced, for example at intervals of between 0.6 and 1.2 cm, preferably at about 1 cm intervals. A spacing of about 1 cm is preferred if the sources are to be implanted for treatment of prostate cancer. Spacer members of suitable lengths are placed between seeds. The number of radioactive seeds used for any particular application will depend on the length of suture member used. Preferably, the radioactive member is provided as a long strip which can then be cut or snapped to the desired length for a particular application by the medical staff.

Preferably, all the radioactive seeds in one suture will contain the same radioisotope and/or be of the same radioactive strength. If more than one type or strength of source is included in one suture, then the different radioactive seeds should be arranged in a regular pattern to allow predictable dosing.

Figure 2:
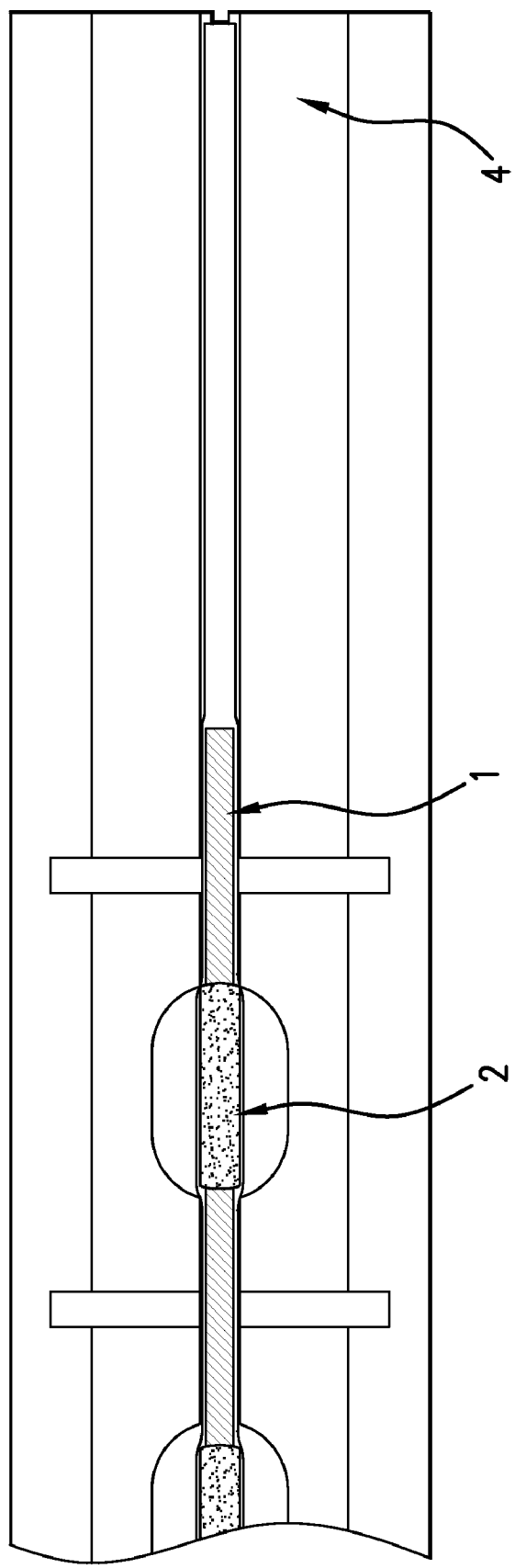
FIG. 2 shows a partial, exploded view of the elongated seed suture member and radioactive seeds located in first and second recesses of a jig member with knife edge slots traversing the first and second recesses.

Preferably, the radioactive member may then be inserted into a jig to form a jig assembly. Such jigs disclosed in U.S. Pat. No. 5,460,592 hereby incorporated by reference. FIG. 2 shows the radioactive seed 2 of the radioactive member and its placement inside a jig 4. The jig 4 allows for a fixed position of the radioactive seeds 2 and spacer members 1, for subsequent manufacturing steps (stiffening), transportation and also for preparation of segments for implant (cutting).

The jig assembly is then dry heated. The dry heat causes the suture member to become rigid. This stiffening process can take place in a process at 160° C. to 190° C. for 60 to 90 minutes.

As a still further feature of the invention there is provided a further method for the production of a radioactive member for use in brachytherapy comprising a hollow elongate bioabsorbable suture member with radioactive seeds and spacer members disposed alternately therein, said method comprising the steps of:
a) providing an elongate preferably single stranded bioabsorbable suture member having a longitudinal groove or slot therein,
b) providing a plurality of radioactive seeds,
c) providing a plurality of bioabsorbable spacer members, wherein the spacer members are of a different color from that of the radioactive seeds and of different diameter from that of the radioactive seeds;
d) placing the radioactive seeds and the spacer members sequentially or concurrently into the groove in the suture member such that the radioactive seeds and the spacer members are securely retained within the groove.

FIG. 5 depicts a member 3 in which the suture includes a slot 9. Seeds 2 and spacers 1 are seen through slot 9. Preferably, the groove or slot will be diametrically opposed to a flat surface of the cross section of the suture. For example, where the suture is substantially round with one flattened surface, the groove or slot will be positioned opposite to this flat surface. This would allow for ease of orientation during manufacture for example, the suture member could be orientated with the slit uppermost using the flat surface for reference so that the sources could be readily pushed into the groove.

Preferably, the groove or slot will be shaped such that once a source is placed therein it is securely retained. For example, the opening to the groove may be slightly narrower than the groove itself and the width of the source such that the source must be "clipped" into place by pushing it through the opening, and is then retained within the groove. For example, a rail or elongate lip may be formed along the long axis of the suture inside the groove and adjacent to the opening of the groove, such that the radioactive seeds and the spacer members, once pushed past the rail or lip, are held in place inside the groove by the rail or lip. Alternatively, a series of suitably spaced protrusions, for example knobs or tabs, may be provided just inside the opening of the groove to hold the sources in place within the groove. Preferably, the rails, lips or protrusions will be formed on both sides of the opening to the groove.

Alternatively or additionally, the radioactive seeds and spacer members may be held in place by a suitable biocompatible adhesive. For example, a bead of a suitable adhesive or resin could be placed in the groove with a source and then the adhesive or resin allowed to dry or a curing method used to dry it. Examples of suitable biocompatible adhesives are known in the art and include epoxy adhesives such as Tra-Bond 2105, a two part epoxy adhesive from Tra-Bond US (see Chem. Eng. News, 8 Dec. 1997, 75 (49) p 40, hereby incorporated by reference); certain tyrosine- and lysine-containing heptapeptides and polypeptides as disclosed in Japanese Patent 05017499, hereby incorporated by reference; certain adhesives derived from polyphenolic proteins as disclosed in U.S. Pat. No. 5,015,677, hereby incorporated by reference; certain dental cement adhesives such as an adhesive composition comprising poly(methyl methacrylate) (PMMA) and 5% of 5-methacryloxyethyl trimellitic anhydride with partially oxidized tibutylborane as disclosed in Proc. IUPAC, I.U.P.A.C., Macromol. Symp., 28$^{th}$ (1982), 395, hereby incorporated by reference; and poly(propyl methacrylate), poly(methyl methacrylate), poly(butyl methacrylate-co-ethyl methacrylate), and silicone gels (see Proc. SPIE-Int. Soc. Opt. Eng, (1998), 3258, 164-168, hereby incorporated by reference).

Alternatively or additionally, the edges of the groove can be deformed or pinched together by application of an external force, for example by applying a compression step in which the upper portion of the groove edges above the widest part of the source are contacted with one or more warmed or heated plates, baffles, flanges or diverting members which may, for example, comprise two plates oriented parallel to the axis of the suture and substantially perpendicular to a projected radius of the radioactive seeds and to each other such that interaction with the groove edges produces a narrowing of the opening in the groove. This can be done after the source is placed in the groove. Alternatively, a rotating heated roller or wheel, configured to apply compression to the grooves in the above manner may be used. The edge of the roller or wheel may be concave to achieve this compression. The compression may be continuous.

Alternatively, heated plates can be used to bend the edges of the groove after a source is placed into the groove. In a grooved opening of a suture material, the edges of the groove can be substantially perpendicular to the base of the groove. The edges of the groove can extend beyond the midpoint of the source, for example beyond the widest part of the source (such as the diameter of a substantially circular source) when viewed from the end of the source when the source is placed into the groove. With the source in the groove, heated plates, baffles, flanges or diverting members can be applied from above or beside the vertical groove edges to contact the vertical edges above the widest part of the source. The heated plates then soften the vertical groove edges and the mechanical force causes the edges to bend over the source, thereby pinching the source in place. Removal of the heated plates allows the bent edges to cool and thenceforth hold the source tightly in place in the grooved suture.

In another embodiment, a heated rotating wheel or roller configured to apply compression to the upper edges of the groove may be used to narrow the opening of a groove after a radioactive seed has been placed therein. A suture with one or more radioactive seeds and spacer members in place within the groove may be fed under a heated rotating wheel or roller, such that part of the wheel or roller contacts the area of the suture adjacent to the opening of the groove, causing it to soften or melt and so deform around the source to hold it in place. Preferably, the part of the roller or wheel contacting the suture will have a concave surface such that the edges of the groove may be deformed or pinched together to form a completely or partially closed tube containing the sources. Contact between a given portion of the suture and the wheel or roller can be temporary as the wheel or roller rotates. Optionally, the suture may be constrained to bend and follow the circumference of the wheel or roller and be held under tension to stretch, compress or further form it.

The suture may be fed under the wheel or roller in a continuous process. Optionally, the part of the wheel or roller contacting the suture may comprise a positive or negative mould such the contact with the suture transfers a reciprocal pattern, for example comprising ridges or bumps, to the suture.

Alternatively or additionally, after loading with radioactive seeds and spacer members, the suture can be encased within a suitable coating, for example of Vicryl™ braid, to hold the radioactive seeds and spacer members in place inside the groove or the discrete openings.

At the end of the manufacturing process, the radioactive member may be cut to suitable lengths and each length loaded separately into a jig, such as the jig disclosed in U.S. Pat. No. 5,460,592. The jig assembly can then be stiffened by a dry heat process as described in a previous embodiment.

Optionally, the radioactive member of the invention will be shielded for shipping from the manufacturing site to the site of use. Preferably, after packaging, the product will be sterilized, for example by any conventional sterilisation procedure such as autoclave, gamma irradiation, ethylene oxide sterilisation or pulse light sterilization. The product can then be shipped from the manufacturer to the site of use as a sterile unit which, once removed from the packaging and shielding, is ready for the member to be used.

The radioactive members of the invention may be used in the treatment of a range of conditions including head and neck cancers (including those of the mouth, lips and tongue) brain tumours, lung tumours, cervical tumours, vaginal tumours and prostate cancer. They may be used as a primary treatment (for example in the treatment of prostate cancer or unresectable tumours) or for treatment of residual disease after excision of the primary tumour. They may be used concurrently with, or at the completion of, other treatment modalities, for example external beam radiation therapy, chemotherapy or hormonal therapy.

The radioactive members of the invention may be used alone or in combination with individual radioactive sources, for example seeds.

As a further aspect of the invention, there is also provided a method of treatment of a condition which is responsive to radiation therapy, for example cancer or arthritis, especially prostate cancer, which comprises the placement of a radioactive member comprising an essentially stiff elongate, single stranded bioabsorbable suture member with spaced radioactive sources disposed therein at or adjacent the site to be treated within a patient for a sufficient period of time to deliver a therapeutically effective dose.

In a preferred embodiment, the radioactive member may be visualised using a suitable imaging technique, preferably ultrasound imaging, in connection with real-time dosimetry equipment.

Figure 3:
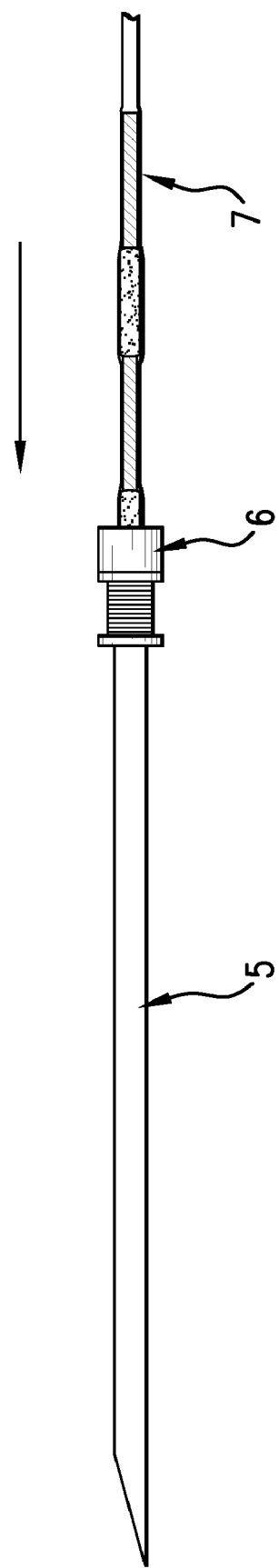
FIG. 3 shows a segment of the prepared radioactive member being loaded into a brachytherapy needle before implantation into a patient.

The radioactive members of the invention may be administered to a patient by placing a suitable length of suture into the tip of a hollow needle and then placing a stylet into the needle, as shown in FIG. 3. The needle 5 may be inserted into a patient and then pulled back over the stylet leaving the suture in place. For methods of administration see, for example, A. van't Riet et al., *Int. J. Radiation Oncology Biol. Phys.*, Vol. 24, pages 555-558, 1992, hereby incorporated by reference.

For example, radioactive member 7 can be prepared to the required length according to the prescribed implant plan. This preparation includes removing the radioactive member from the packaging and sterility barrier and cutting through a spacer member to the prescribed length. The radioactive member, cut to the prescribed length, is then inserted into an insertion needle, through a hub end 6 thereof, to the point where the entire assembly is completely inside the needle 5. The radioactive member is then pushed through the hollow insertion needle, with a needle stylet, until the leading tip of the radioactive member reaches a needle plugging media, such as bone wax. The loaded insertion needle is then inserted into a prescribed treatment area of a patient, for example, prostate. The insertion needle is subsequently removed, leaving the radioactive member in the prescribe treatment area. The radioactive member is provided sterile for immediate preparation and use.

Figure 4:
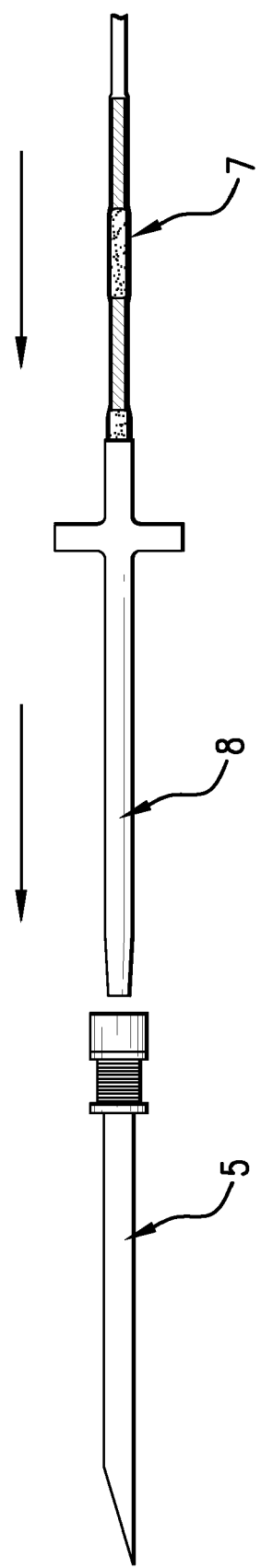
FIG. 4 shows a segment of the prepared device being loaded into a after-loading device and then into a brachytherapy needle at the time of implantation into a patient.

An alternate method of insertion needle loading would include the use of an after-loading device, as shown in FIG. 4. In this embodiment, the insertion needle 5 can be inserted into the prescribed treatment area of a patient, for example, prostate, in advance of loading the radioactive member, following the pre-operative implant plan. The radioactive member 7, prepared to the prescribed length, is then loaded into an after-loading device 8, which temporarily houses the radioactive member. When required, the radioactive member is then transferred to the insertion needle where it mates into the insertion needle hub. A stylet is then used to advance the radioactive member through the after-loading device, into the needle, and finally into the patient.

The invention described and claimed herein is not to be limited in scope by the specific embodiments herein disclosed, since these embodiments are intended as illustration of several aspects of the invention. Any equivalent embodiments are intended to be within the scope of this invention.

Indeed, various modifications of the invention in addition to those shown and described herein will become apparent to those skilled in the art from the foregoing description. Such modifications are also intended to fall within the scope of the appended claims.

What is claimed is:

1. A method for the production of a radioactive member for use in brachytherapy comprising an elongate, bioabsorbable suture member with radioactive seeds and spacer members disposed alternately therein, said method comprising the steps of:
   a) providing a hollow bioabsorbable suture member and a plurality of radioactive seeds and
      a plurality of bioabsorbable spacer members within the suture member, wherein the spacer members are dyed with a different color from that of the undyed radioactive seeds and of different diameter from that of radioactive seeds and wherein the sources and spacer members are alternately placed into the suture member in a predetermined pattern;
   b) heating the radioactive sources to a temperature above the softening temperature of the suture material wherein said heating allows coloration to transfer from the spacer members to the suture member; and
   f) cooling the suture member such that it solidifies or hardens about each source and spacer member so as to securely retain each source in place.

2. A method of claim 1, wherein the diameter of the spacer member is 0.1 mm to 0.5 mm smaller than that of the radioactive seeds.

3. A method of claim 1, wherein the color of the spacer member is dyed with violet.

4. A method of claim 1, further comprising a step of sterilizing the radioactive member.

5. A method for the production of a radioactive member for use in brachytherapy comprising a hollow elongate bioabsorbable suture member with radioactive seeds and spacer members disposed alternately therein, said method comprising the steps of:
   a) providing an elongate preferably single stranded bioabsorbable suture member which is at a temperature above its softening temperature,
   b) providing a plurality of radioactive seeds,
   c) providing a plurality of bioabsorbable spacer members, wherein the seeds and spacers are positioned within the suture member and wherein the spacer members dyed with a different color from that of the undyed radioactive seeds and of different diameter from that of the radioactive seeds;
   d) heating the suture member to a temperature above the softening temperature of the suture member, wherein said heating step allows coloration to transfer from the spacer members to the suture member;
   e) cooling the suture member such that it solidifies or hardens about each source and spacer member so as to securely retain each radioactive seeds and spacer member in place.

6. A method for the production of a radioactive member for use in brachytherapy comprising a hollow elongate bioabsorbable suture member with radioactive seeds and spacer members disposed alternately therein, said method comprising the steps of:
   a) providing an elongate preferably single stranded bioabsorbable suture member having a longitudinal groove or slot therein;
   b) providing a plurality of radioactive seeds,
   c) providing a plurality of bioabsorbable spacer members, wherein the spacer members dyed with a different color from that of the undyed radioactive seeds and of different diameter from that of the radioactive seeds;
   d) placing the radioactive seeds and the spacer members sequentially or concurrently into the groove in the suture member such that the radioactive seeds and the spacer members are securely retained within the groove; and
   e) heat sealing the groove to retain the seeds and spacers therein, wherein said heat sealing step allows coloration to transfer from the spacer members to the suture member.

7. A method as claimed in claim 6 wherein the radioactive seeds and the spacer members are retained in the groove using a biocompatible adhesive or resin.

8. A method as claimed in claim 6 wherein the radioactive seeds and the spacer members are retained in the groove by means of one or more rails, lips, tabs or knobs.

9. A method of claim 6, wherein it further comprises a step of providing means to apply an external force to deform the edges of the groove around the radioactive seeds and the spacer members such that each radioactive seed and spacer member are securely retained in the groove.

10. A method of claim 9, wherein the means comprises a heated plate, baffle, flange, wheel or roller.

11. A method of claim 10 wherein the means comprises a concave surface.

* * * * *